(12) United States Patent
Lovell

(10) Patent No.: US 7,575,581 B2
(45) Date of Patent: Aug. 18, 2009

(54) DEVICE FOR HOLDING AND INSERTING ONE OR MORE COMPONENTS OF A PEDICLE SCREW ASSEMBLY

(75) Inventor: John Robert Lovell, North Bergen, NJ (US)

(73) Assignee: Blackstone Medical, Inc., Springfield, MA (US)

( * ) Notice: Subject to any disclaimer, the term of this patent is extended or adjusted under 35 U.S.C. 154(b) by 0 days.

(21) Appl. No.: 11/608,156

(22) Filed: Dec. 7, 2006

(65) Prior Publication Data

US 2007/0233155 A1    Oct. 4, 2007

Related U.S. Application Data

(60) Provisional application No. 60/748,333, filed on Dec. 7, 2005.

(51) Int. Cl.
*A61B 17/60* (2006.01)
(52) U.S. Cl. .......................................... 606/104; 81/453
(58) Field of Classification Search ............... 606/86 R, 606/86–89, 86 A, 99, 914, 916; 81/453, 81/451, 448; 269/3, 6; 29/255, 278
See application file for complete search history.

(56) References Cited

U.S. PATENT DOCUMENTS

| | | | | |
|---|---|---|---|---|
| 2,292,657 A * | 8/1942 | Priest | ........................ | 81/453 |
| 2,519,811 A * | 8/1950 | Alexander | ................... | 81/454 |
| 2,634,641 A * | 4/1953 | Hodges | ........................ | 81/113 |
| 3,373,639 A * | 3/1968 | Dalen et al | ..................... | 81/112 |
| 4,210,145 A * | 7/1980 | Nestor et al. | ................. | 606/172 |
| 5,209,753 A * | 5/1993 | Biedermann et al. | ......... | 606/304 |
| 5,217,486 A * | 6/1993 | Rice et al. | .................... | 606/232 |
| 5,423,825 A * | 6/1995 | Levine | ...................... | 606/86 R |
| 5,667,513 A * | 9/1997 | Torrie et al. | .................. | 606/104 |
| 5,993,459 A * | 11/1999 | Larsen et al. | ................ | 606/104 |
| 6,123,707 A | 9/2000 | Wagner | | |
| 6,440,133 B1 * | 8/2002 | Beale et al. | ................ | 606/86 A |
| 7,073,415 B2 * | 7/2006 | Casutt et al. | ................... | 81/451 |
| 7,090,680 B2 * | 8/2006 | Bonati et al. | ................. | 606/104 |
| 7,226,453 B2 * | 6/2007 | Chao et al. | .................... | 606/104 |
| 7,326,211 B2 * | 2/2008 | Padget et al. | ................... | 606/67 |
| 2005/0085813 A1 | 4/2005 | Spitler et al. | | |
| 2005/0131408 A1 | 6/2005 | Sicvol et al. | | |
| 2005/0131421 A1 | 6/2005 | Anderson et al. | | |
| 2005/0131422 A1 | 6/2005 | Anderson et al. | | |

OTHER PUBLICATIONS

Spinal Concepts, Path Finder, "Minimally Invasive Spinal Fixation".

* cited by examiner

*Primary Examiner*—Eduardo C Robert
*Assistant Examiner*—James L Swiger
(74) *Attorney, Agent, or Firm*—Kenyon & Kenyon LLP

(57) ABSTRACT

The present invention relates to a device (and corresponding method) for holding and inserting one or more components of a pedicle screw assembly. In one example (which example is intended to be illustrative and not restrictive), the present invention may be used in connection with minimally invasive surgery.

20 Claims, 15 Drawing Sheets

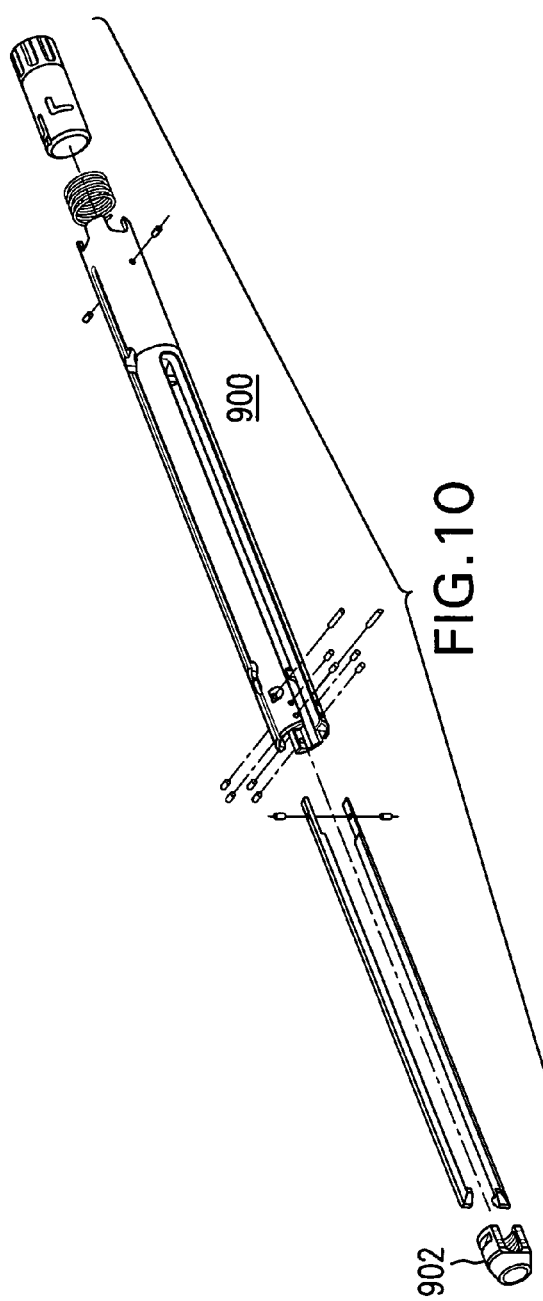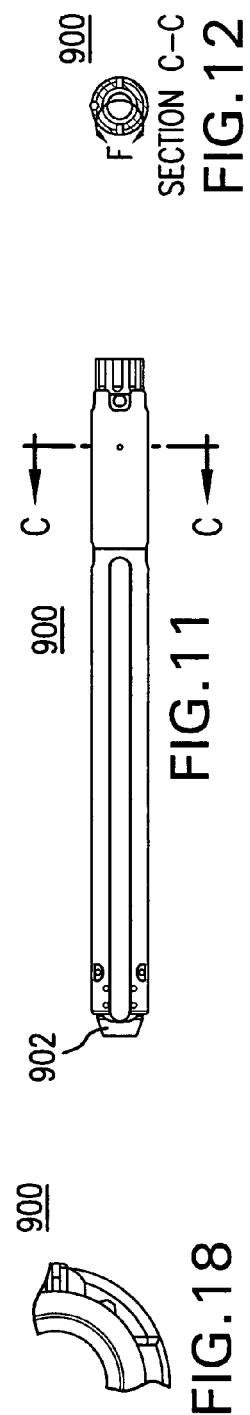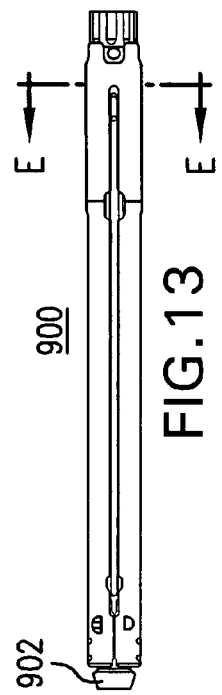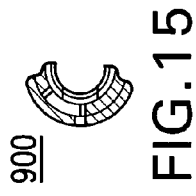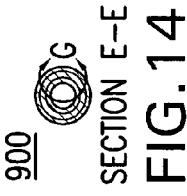

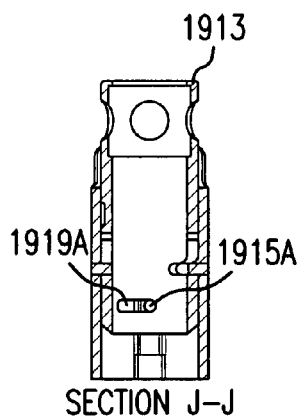
FIG. 28 SECTION J-J
FIG. 29
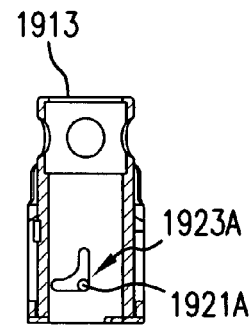
FIG. 33
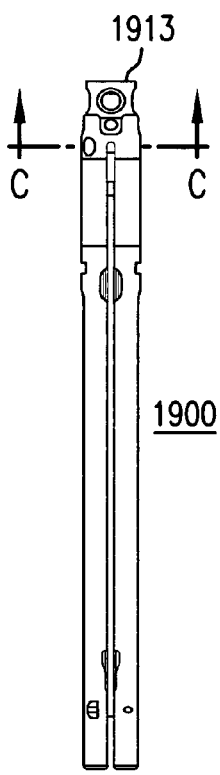
FIG. 25
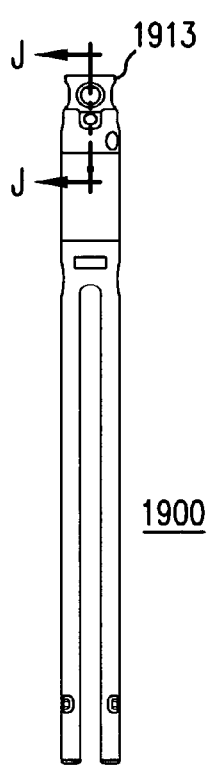
FIG. 27
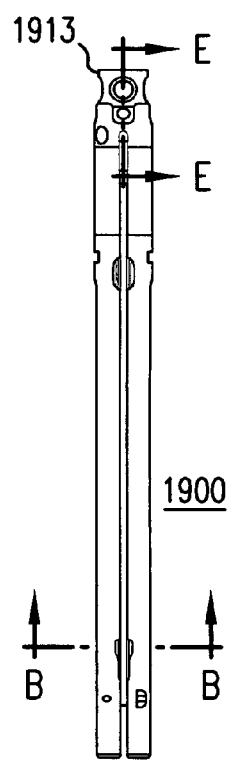
FIG. 31
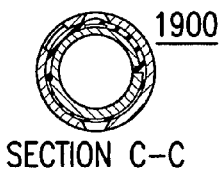
FIG. 26 SECTION C-C
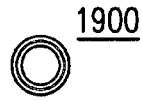
FIG. 30
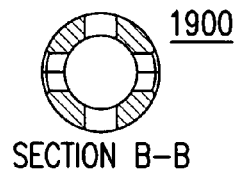
FIG. 32 SECTION B-B

DEVICE FOR HOLDING AND INSERTING ONE OR MORE COMPONENTS OF A PEDICLE SCREW ASSEMBLY

CROSS-REFERENCE TO RELATED APPLICATIONS

This application claims priority to and the benefit of U.S. Provisional Application Ser. No. 60/748,333, filed Dec. 7, 2005, the entirety of which is incorporated herein by reference.

FIELD OF THE INVENTION

The present invention relates to a device (and corresponding method) for holding and inserting one or more components of a pedicle screw assembly.

In one example (which example is intended to be illustrative and not restrictive), the present invention may be used in connection with minimally invasive surgery.

BACKGROUND OF THE INVENTION

Spinal fixation has conventionally been carried out using one or more spinal rods held in place adjacent a patient's spine through the use of a number of pedicle screw assemblies. In this regard, a conventional pedicle screw assembly typically includes a bone screw (driven into the pedicle) and a receiver element (or head) mated thereto (e.g., mated in such a manner as to permit multi-axial positioning). Further, the receiver element is typically configured to receive and hold the spinal rod.

BRIEF DESCRIPTION OF THE DRAWINGS

FIGS. 9-18 show various views of a device according to another embodiment of the present invention (wherein FIG. 9 is a perspective view; FIG. 10 is an exploded perspective view; FIG. 11 is a side view; FIG. 12 is a section along line C-C of FIG. 11; FIG. 13 is another side view (offset 90 degrees from the side view of FIG. 11); FIG. 14 is a section along line E-E of FIG. 13; FIG. 15 shows detail "F" from FIG. 12; FIG. 16 shows detail "G" from FIG. 14; FIG. 17 is a distal end view of the device shown in FIG. 13; and FIG. 18 shows detail "A" from FIG. 17;

FIGS. 19-37 show various views of a device according to another embodiment of the present invention (wherein FIG. 19 is a perspective view; FIG. 20 is an exploded perspective view; FIG. 21 is a side view; FIG. 22 is a section along line A-A of FIG. 22 (showing detail of the distal end of the device); FIG. 23 is another view showing detail of the distal end of the device (wherein the device is in a closed state); FIG. 24 is another view (in partial cross-section) showing detail of the distal end of the device (wherein the device is in an open state); FIG. 25 is another view of the device showing the knob in an unlocked state; FIG. 26 is a section along line C-C of FIG. 25; FIG. 27 is another view of the device showing the knob in an unlocked state; FIG. 28 is a section along line J-J of FIG. 27; FIGS. 29 and 30 show, respectively, a proximal end and a distal end view of the device of FIG. 27; FIG. 31 is another view of the device showing the knob in an unlocked state; FIG. 32 is a section along line B-B of FIG. 31; FIG. 33 is a section along line E-E of FIG. 31; FIG. 34 is another view of the device showing the knob in a locked state; FIG. 35 is a section along line D-D of FIG. 34; FIG. 36 is a section along line H-H of FIG. 34; and FIG. 37 is another view of the device showing the knob in a locked state;

FIG. 38B is a side view; FIG. 38C is another side view (offset 90 degrees from the side view of FIG. 38B); FIG. 38D is a top view; and FIG. 38E is a bottom view).

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Figure 1:
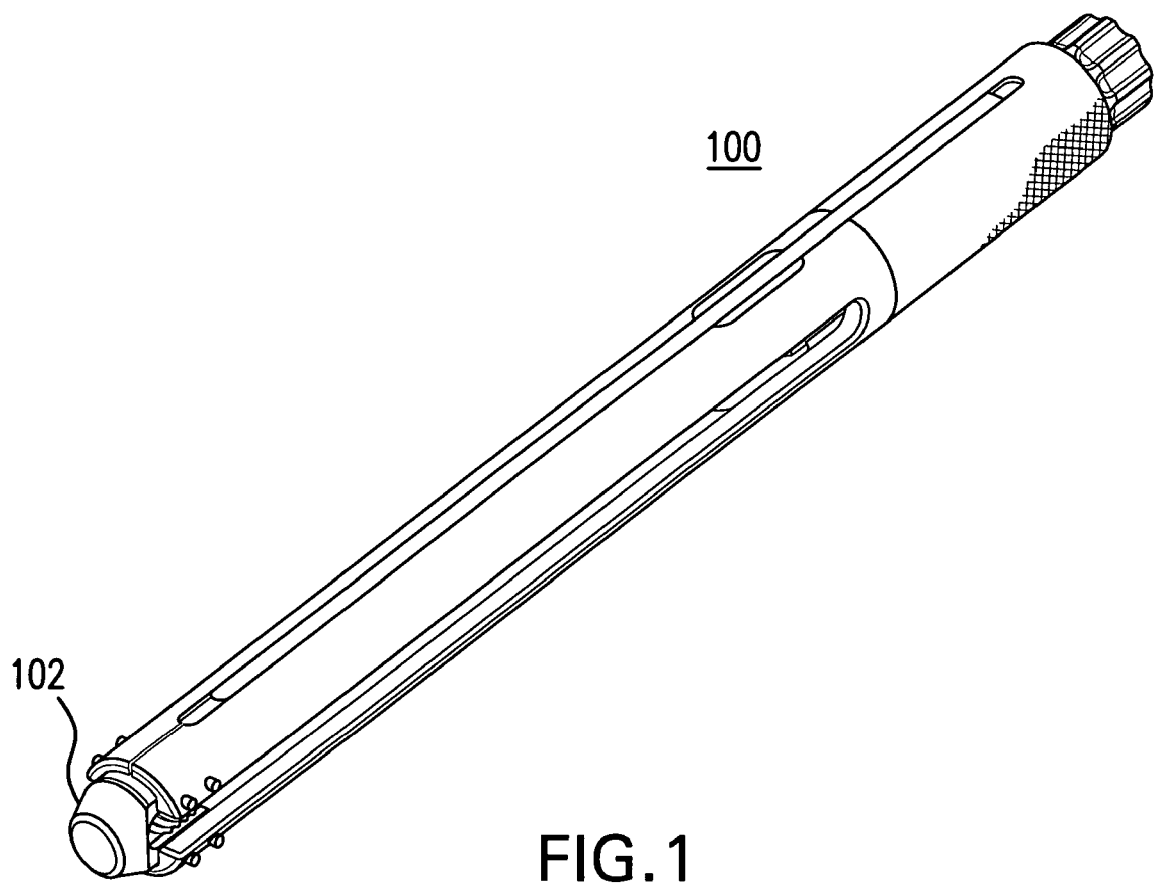
FIG. 1 shows a perspective view of a device according to an embodiment of the present invention.

Referring now to FIG. 1, a perspective view of a device according to an embodiment of the present invention used for holding and percutaneously inserting a receiver element of a pedicle screw assembly is shown. More particularly, Holder 100 is configured to hold and releasably insert Receiver Element 102 of the pedicle screw assembly (of note, other parts of the pedicle screw assembly (such as the bone screw itself) are not shown in the Figures).

Figure 2:
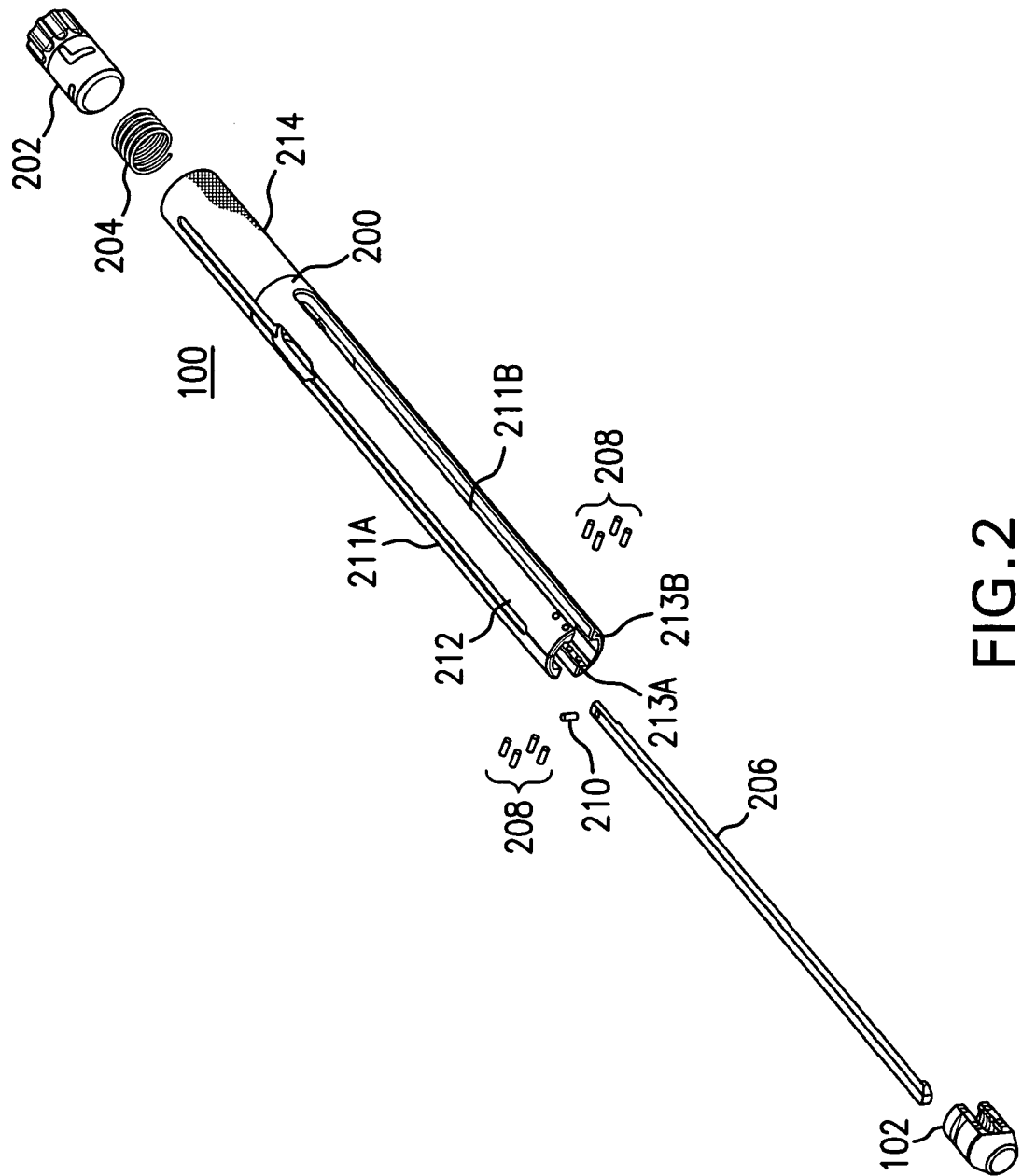
FIG. 2 shows an exploded perspective view of the device of FIG. 1

Referring now to FIG. 2, an exploded perspective view of the device of FIG. 1 is shown. More particularly, it is seen that Holder 100 includes Body 200, Lock/Unlock Knob 202, Compression Spring 204, Sliding Wedges 206, Retention Pins 208 and Wedge/Knob Mating Pins 210. Of note, two Sliding Wedges 206 are utilized in this embodiment, although this FIG. 2 only shows one of such Sliding Wedges 206 and one of such Wedge/Knob Mating Pins 210. Further, Body 200 includes a first blade set (comprising Blades 211A and 211B), a second blade set (comprising Blades 213A and 213B), Wedge Openings 212 (only one is seen in this view) and Knurled Surface 214.

Each of Sliding Wedges 206 may be slidable within a corresponding groove formed at the interface of Blades 211A and 211B of the first blade set and Blades 213A and 213B of the second blade set.

In any case, in operation each Sliding Wedge 206, when moved forward by depression of the Lock/Unlock Knob 202, wedges a respective one of Blade 211A and 211B (in the case of the first blade set) and Blade 213A and 213B (in the case of the second blade set) open to release Receiver Element 102 therefrom (as discussed in greater detail below, Receiver Element 102 may be held via Retention Pins 208 being biased into corresponding holes in Receiver Element 102 (e.g., in an exterior surface of Receiver Element 102)).

Figure 3:
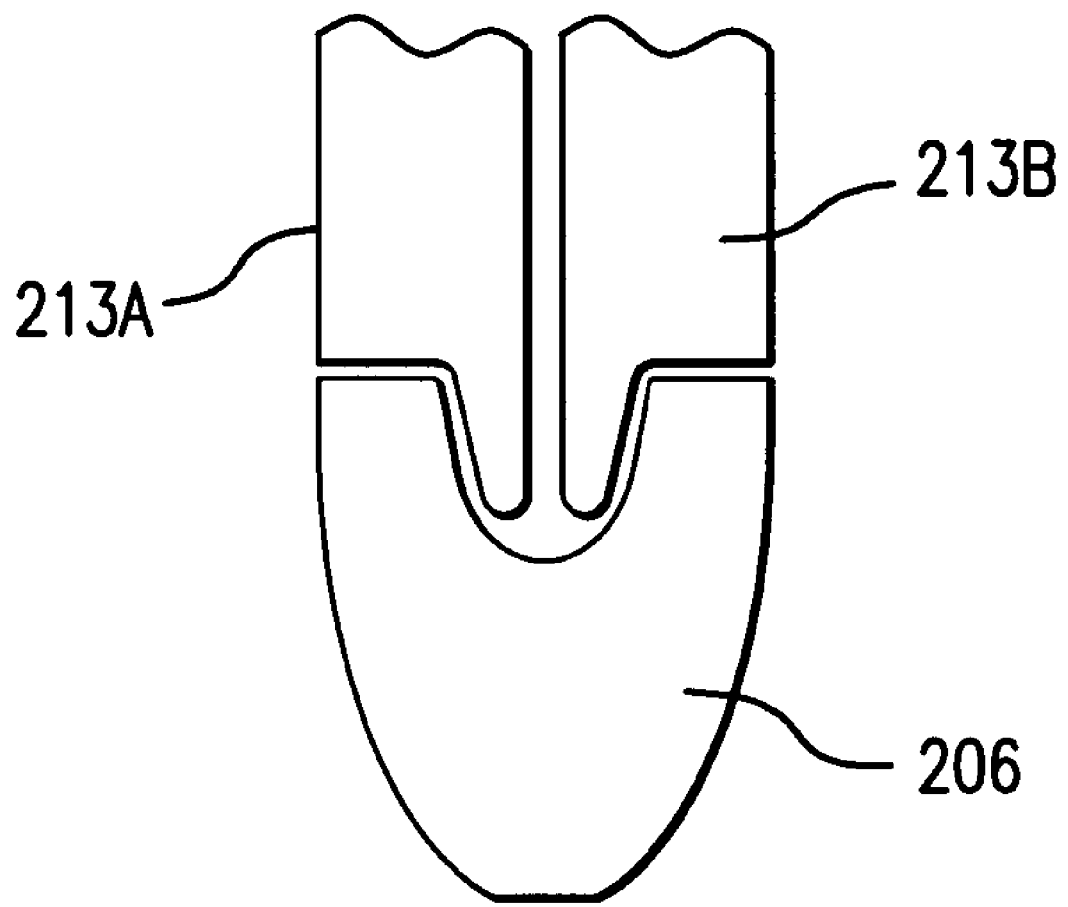
FIG. 3 shows certain details of the device of FIG. 1.

Of note, one or more features (e.g., on the underside of each Sliding Wedge 206) may keep Blades 211A and 211B (in the case of the first blade set) and Blades 213A and 213B (in the case of the second blade set) parallel (locked) until Lock/Unlock Knob 202 is slid forward (see, e.g., FIG. 3).

Figure 4A:
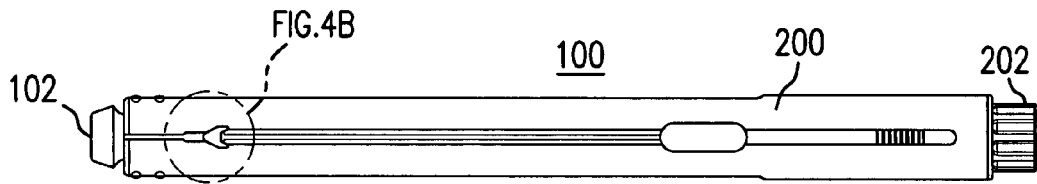
FIG. 4A shows a side view of the device of FIG. 1
Figure 4B:
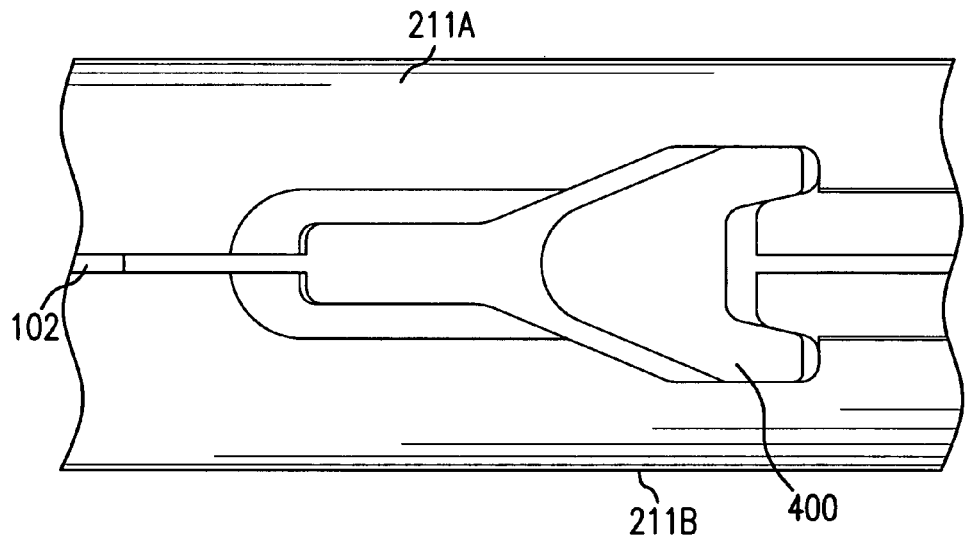
FIG. 4B shows a detail view of the distal end of the device.

Referring now to FIGS. 4A and 4B, a side view of the device of FIG. 1 is shown (FIG. 4A) along with a detail view of the distal end of the device (FIG. 4B). More particularly, it is seen that Locking Feature 400 (associated with each of Sliding Wedges 206) prevents Blades 211A and 211B (in the case of the first blade set) and Blades 213A and 213B (in the case of the second blade set) from opening and releasing Receiver Element 102 (when driven forward, Sliding Wedges 206 function to open Blades 211A and 211B (in the case of the first blade set and Blades 213A and 213B (in the case of the second blade set) and release Receiver Element 102). Of note, this FIG. 4B depicts the locked position.

Figure 5A:
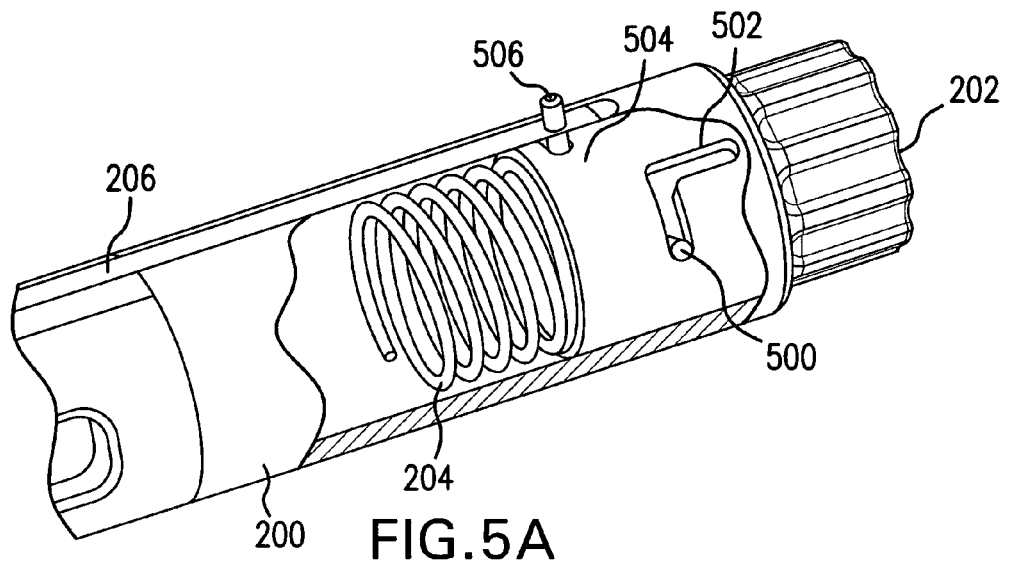
FIGS. 5A-5C show certain details regarding the proximal end of the device of FIG. 1.
Figure 5B:
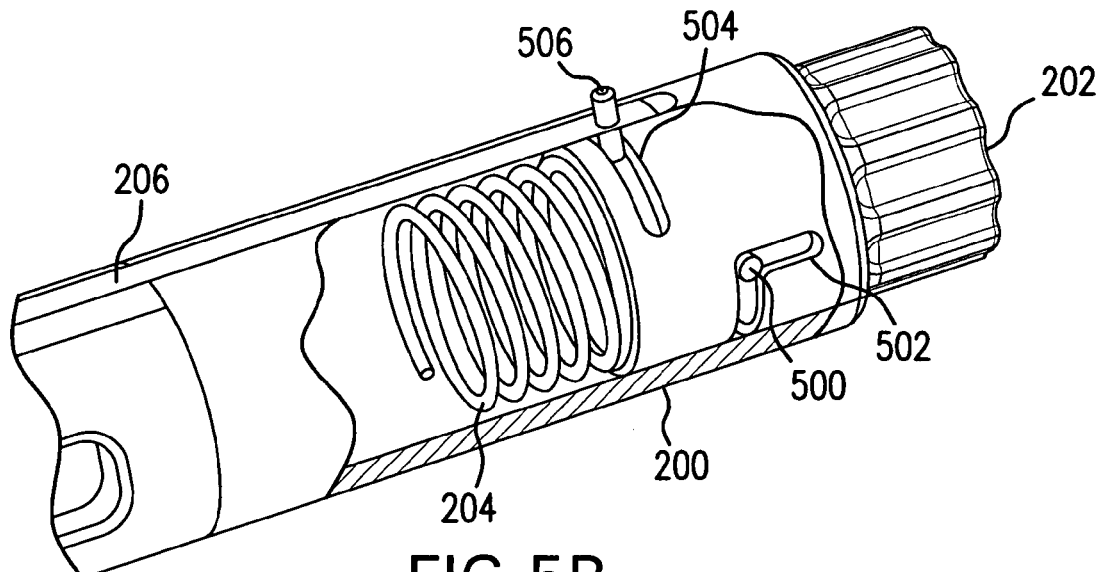
Figure 5C:
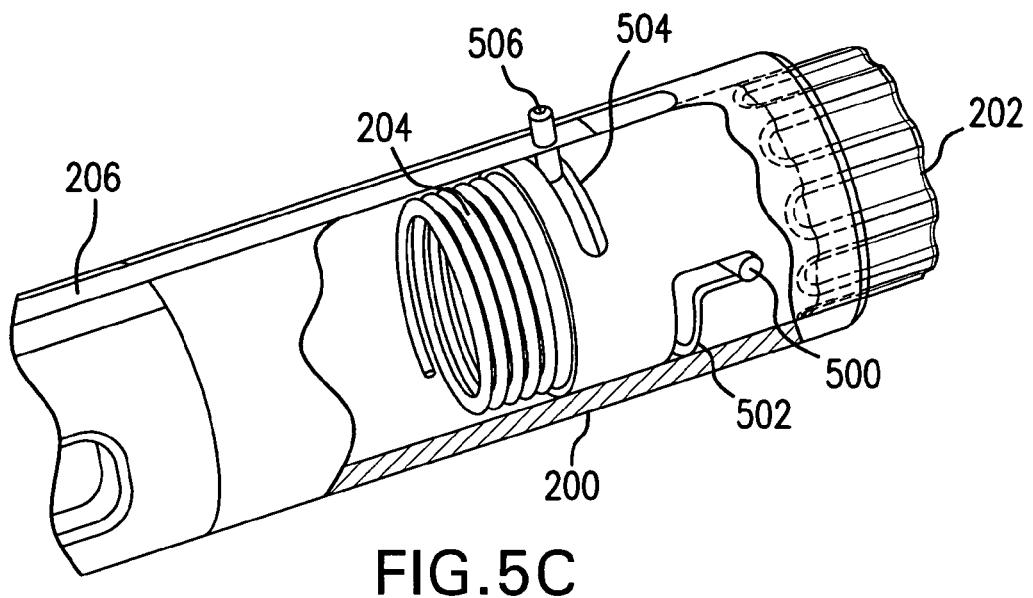

Referring now to FIGS. 5A-5C, certain details regarding the proximal end of Holder 100 are shown. More particularly, it is seen in these Figures. that when Lock/Unlock Knob 202 is locked as shown in FIG. 5A, each Sliding Wedge 206 is held in the position depicted in FIG. 4B. In this position, the Receiver Element 102 is captured and can not be released. Further, Lock Pin 500 prevents Lock/Unlock Knob 202 from moving axially along First Knob Slot 502.

Referring now more particularly to FIG. 5B, it is seen that Lock/Unlock Knob 202 has been rotated to allow Lock/Unlock Knob 202 to travel along the axis of Body 100 due to the keyway in First Knob Slot 502.

Referring now more particularly to FIG. 5C, it is seen that Lock/Unlock Knob 202 is depressed, causing Second Knob Slot 504 to drive Sliding Wedge 206 forward (via Pin 506 pressed into Sliding Wedge 206). Of course, in the position of this FIG. 5C, Spring 204 is compressed relative to the positions of FIG. 5A and 5B.

Figure 6:
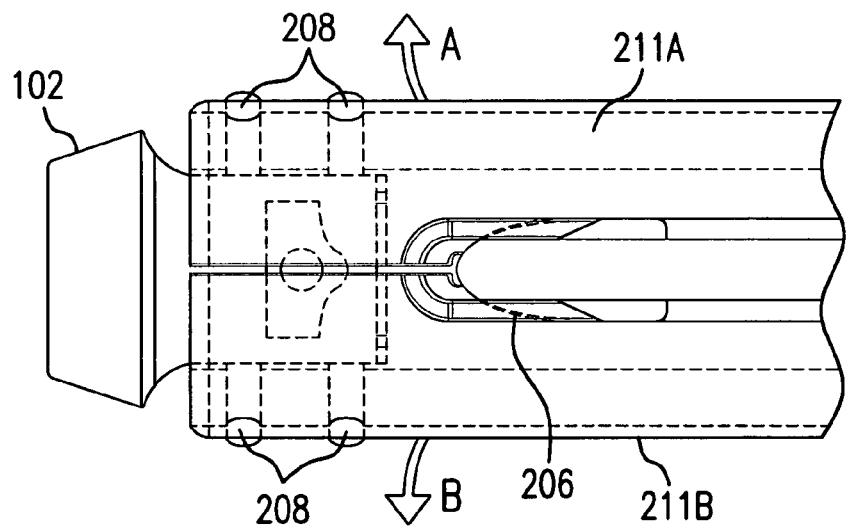
FIG. 6 shows certain details regarding the distal end of the device of FIG. 1.

Referring now to FIG. 6, it is seen that when Lock/Unlock Knob 202 is depressed (as in FIG. 5C), Blades 211A and 211B (in the case of the first blade set) and Blades 213A and 213B (in the case of the second blade set) will be driven apart (e.g., along arrows A and B), allowing Pins 208 to release Receiver Element 102 (Receiver Element 102 includes holes therein corresponding to each of Pins 208). Of note, Blades 211A and 211B (in the case of the first blade set) and Blades 213A and 213B (in the case of the second blade set) are shown in this Fig. as having essentially planar inner faces, although in another example Blades 211A and 211B (in the case of the first blade set) and Blades 213A and 213B (in the case of the second blade set) may have angled inner faces to correspond to Sliding Wedges 206 and to allow Blades 211A and 211B (in the case of the first blade set) and Blades 213A and 213B (in the case of the second blade set) to be forced apart.

Figure 7:
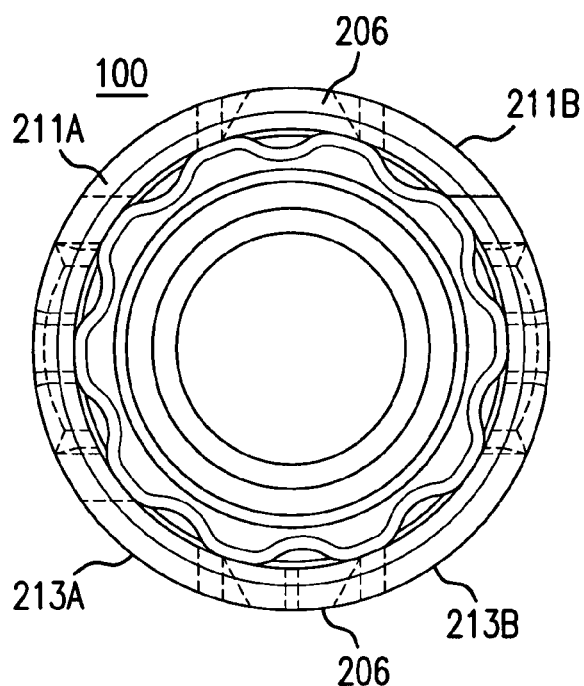
FIG. 7 shows certain details regarding the distal end of the device of FIG. 1.

Referring now to FIG. 7, an end view of the distal end of Holder 100 is shown. More particularly, it is seen in this FIG. that each Sliding Wedge 206 may be dovetailed to prevent pop-out when Blades 211A and 211B (in the case of the first blade set) and Blades 213A and 213B (in the case of the second blade set) are wedged apart.

Figure 8:
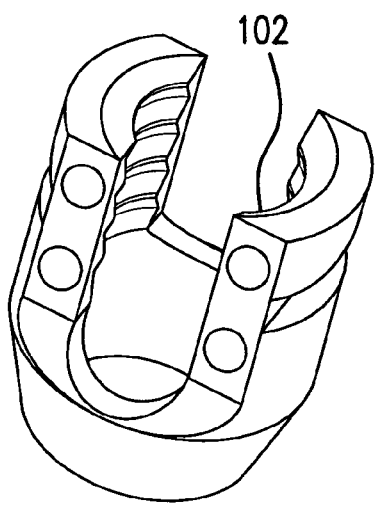
FIG. 8 shows a receiver element of the type which may be held by the device of FIG. 1.

Referring now to FIG. 8, a perspective view of Receiver Element 102 is shown.

Figure 9:
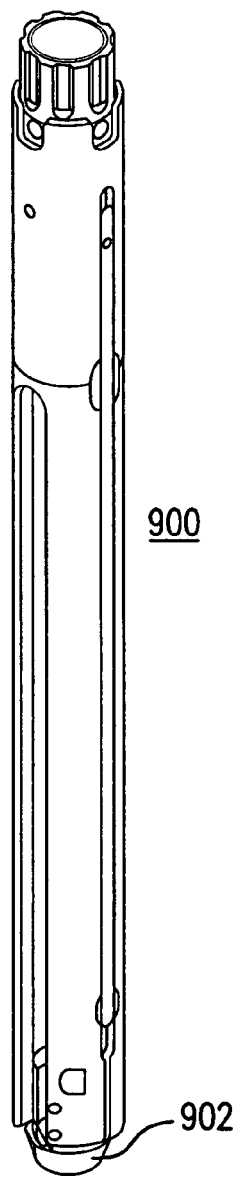
Figure 16:
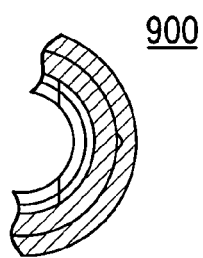

Referring now to FIGS. 9-18, various views of a device according to another embodiment of the present invention are shown. More particularly, FIG. 9 shows a perspective view of Holder 900 (holding Receiver Element 902); FIG. 10 shows an exploded perspective view of Holder 900 of FIG. 9; FIG. 11 shows a side view of Holder 900 of FIG. 9 (holding Receiver Element 902); FIG. 12 shows a cross-section of Holder 900 taken along line C-C of FIG. 11; FIG. 13 shows another side view (offset 90 degrees from the view of FIG. 11) of Holder 900 of FIG. 9 (holding Receiver Element 902); FIG. 14 shows a cross-section of Holder 900 taken along line E-E of FIG. 13; FIG. 15 shows detail "F" of FIG. 12; FIG. 16 shows detail "G" of FIG. 14; FIG. 17 shows a distal end view of Holder 900; and FIG. 18 shows detail "A" of FIG. 17.

Figure 19:
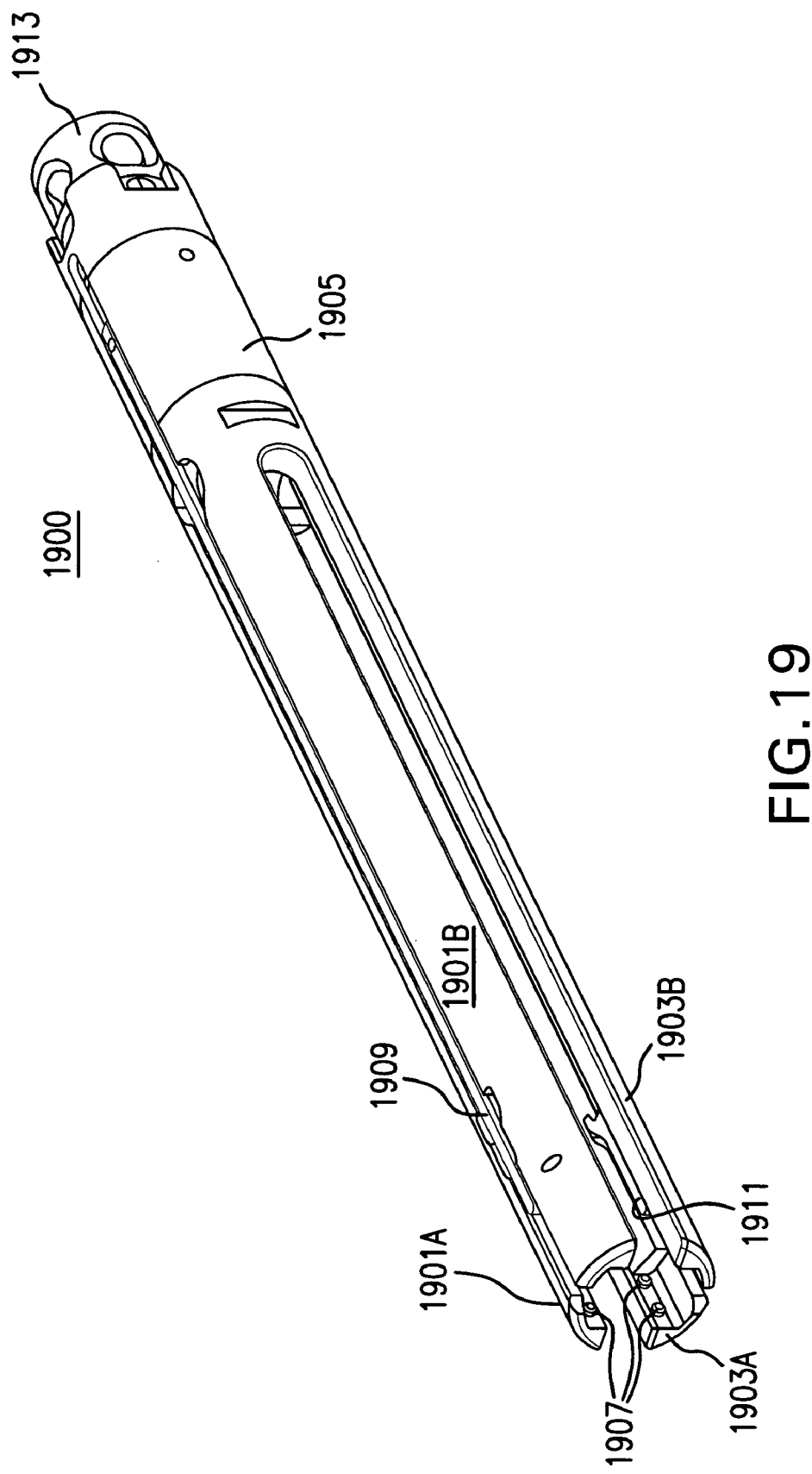
Figure 20:
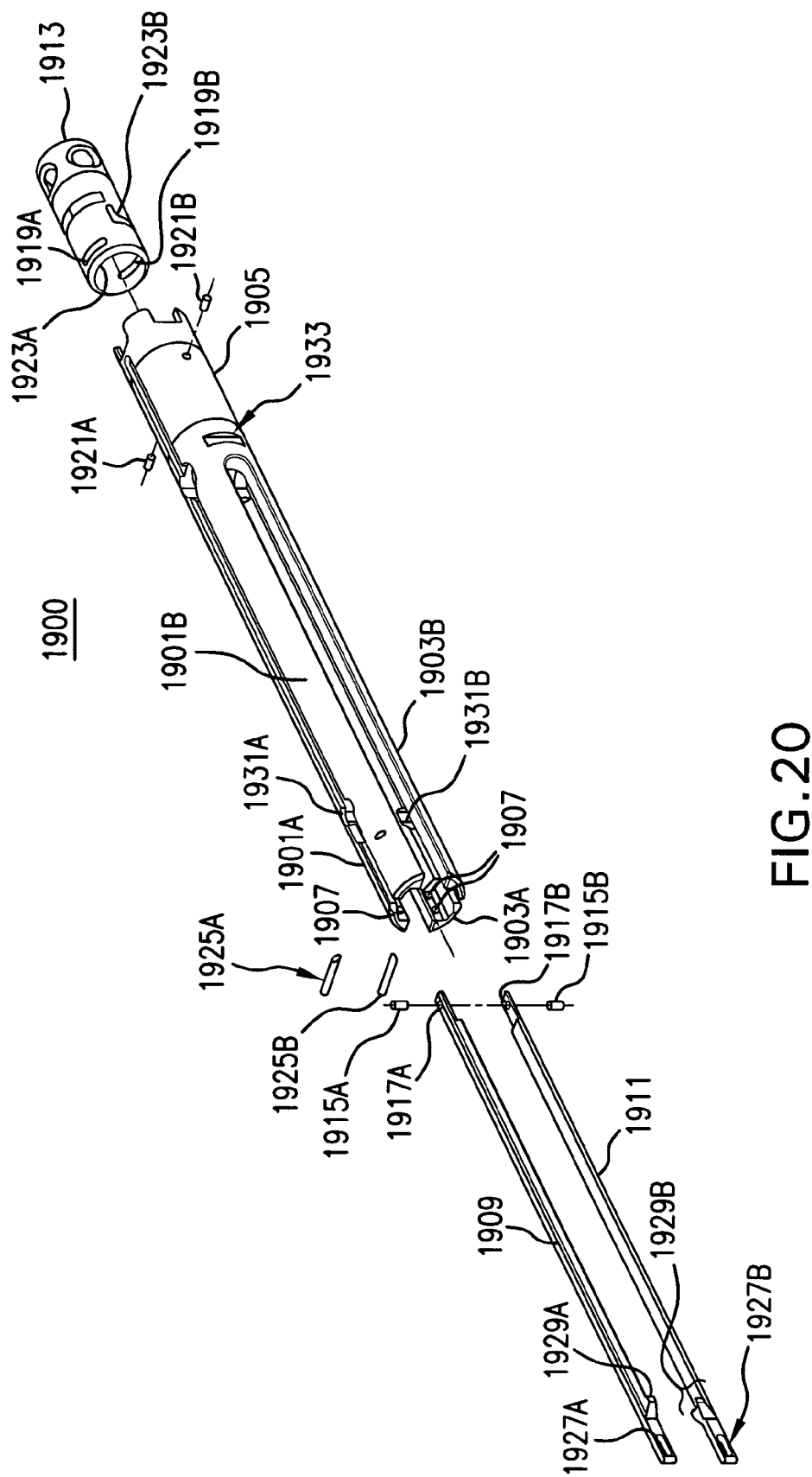
Figure 21:
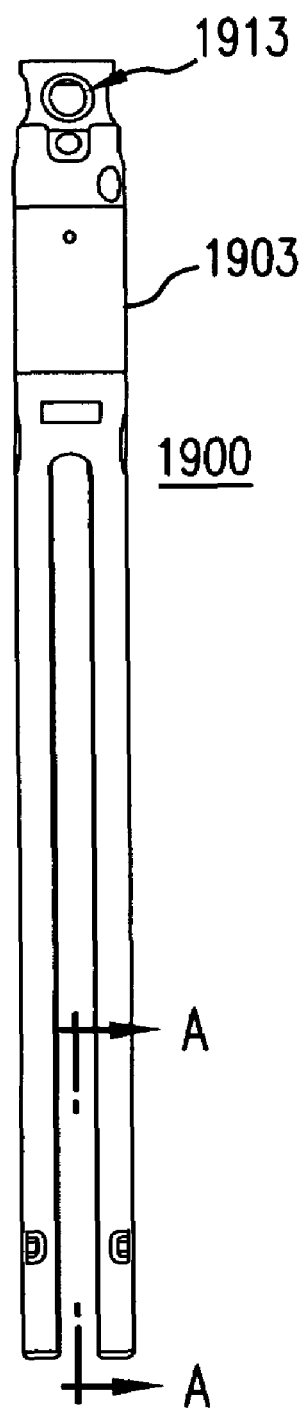
Figure 22:
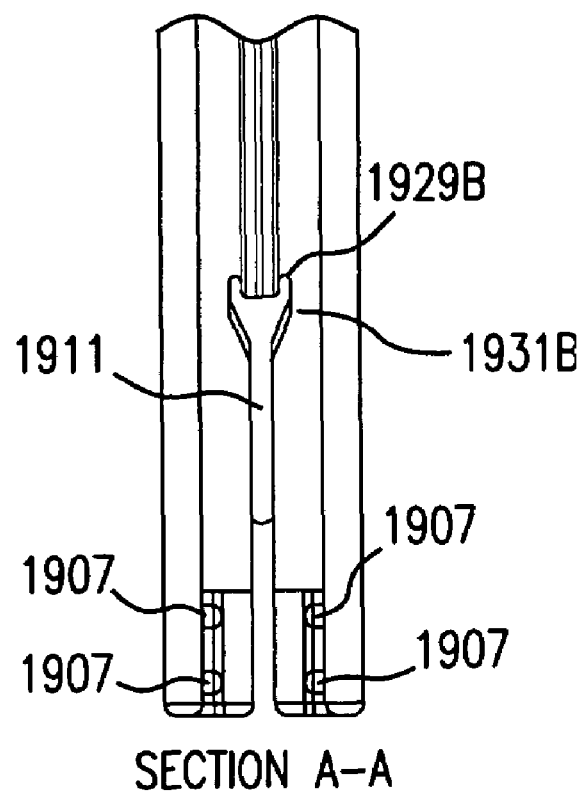
Figure 23:
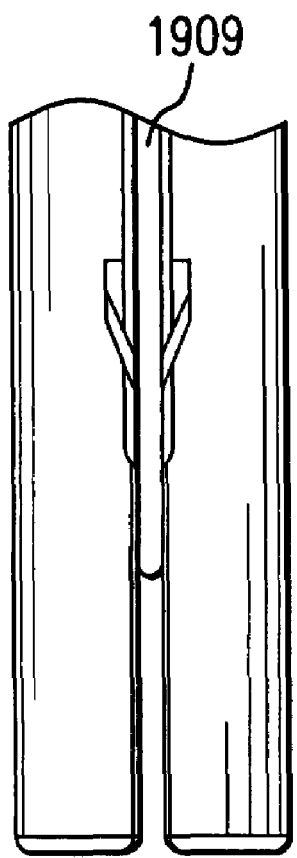
Figure 24:
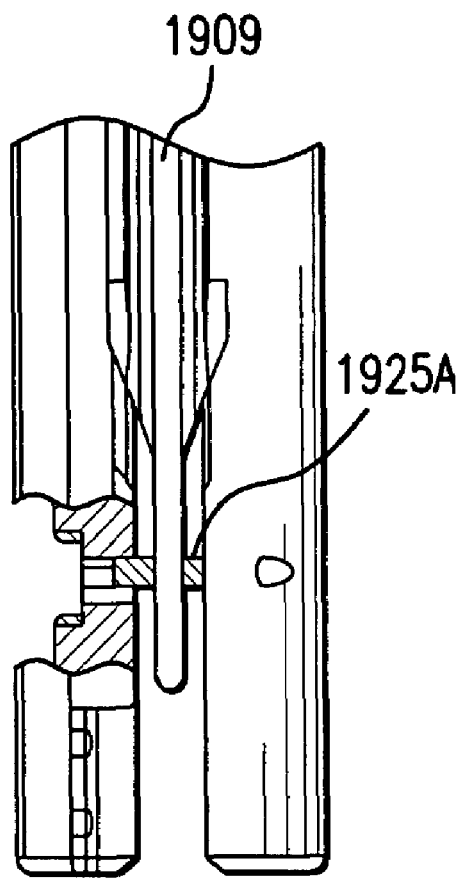
Figure 34:
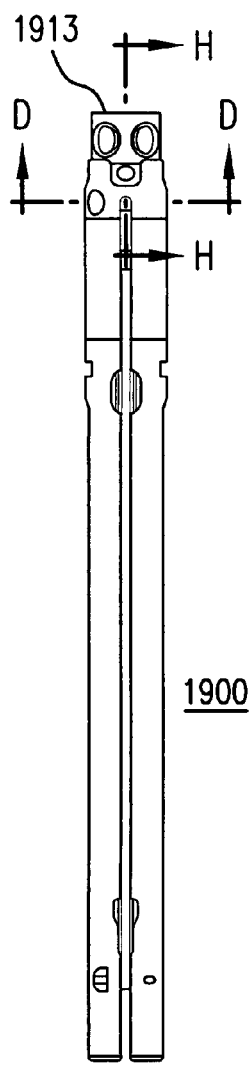
Figure 36:
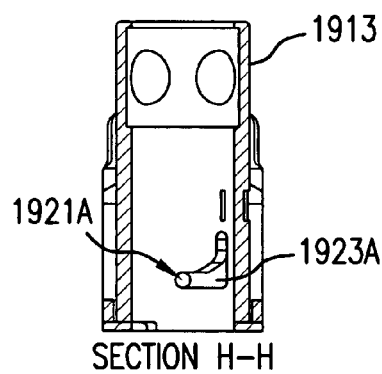
Figure 37:
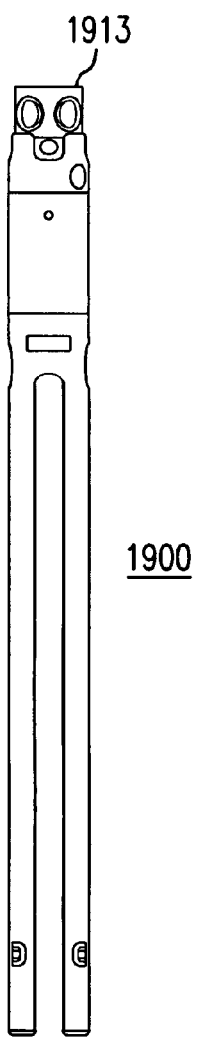
Figure 35:
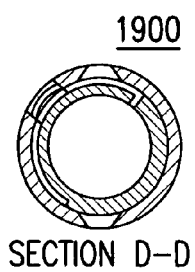
Figure 38D:
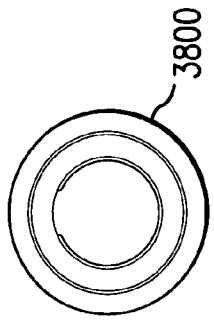
FIGS. 38A-38E show various views of a pedicle screw receiver element according to another embodiment of the present invention (wherein FIG. 38A is a perspective view.
Figure 38C:
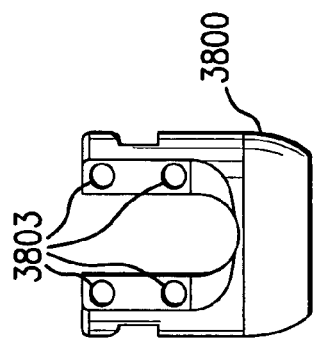
Figure 38E:
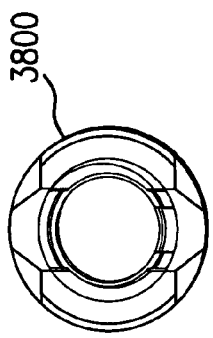
Figure 38B:
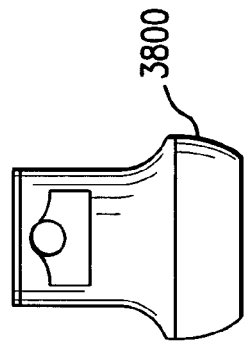
Figure 38A:
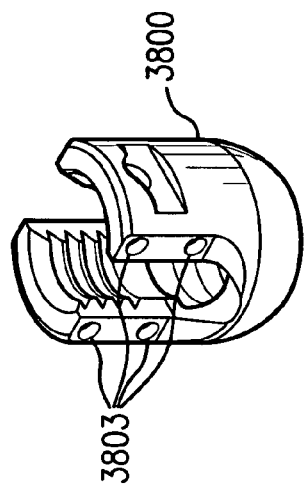

Referring now to FIGS. 19-37, various views of an apparatus for releasably holding a receiver element of a pedicle screw assembly according to another embodiment of the present invention are shown. More particularly, FIG. 19 shows a perspective view of Holder 1900; FIG. 20 shows an exploded view of Holder 1900 of FIG. 19; FIG. 21 shows a side view of Holder 1900 of FIG. 19; FIG. 22 shows a cross-section of Holder 1900 taken along line A-A of FIG. 21; FIG. 23 shows detail of the distal end of Holder 1900 in a "relaxed" or "normal" state (i.e., in a state in which the wedges do not bias the blades open); FIG. 24 shows detail of the distal end of Holder 1900 in an "actuated" state (i.e., in a state in which the wedges do bias the blades open); FIG. 25 is another view of the device showing the knob in an unlocked state; FIG. 26 is a section along line C-C of FIG. 25; FIG. 27 is another view of the device showing the knob in an unlocked state; FIG. 28 is a section along line J-J of FIG. 27; FIGS. 29 and 30 show, respectively, a proximal end and a distal end view of the device of FIG. 27; FIG. 31 is another view of the device showing the knob in an unlocked state; FIG. 32 is a section along line B-B of FIG. 31; FIG. 33 is a section along line E-E of FIG. 31; FIG. 34 is another view of the device showing the knob in a locked state; FIG. 35 is a section along line D-D of FIG. 34; FIG. 36 is a section along line H-H of FIG. 34; and FIG. 37 is another view of the device showing the knob in a locked state.

Still referring to FIGS. 19-37, it is seen in these Figures. that Holder 1900 includes Blades 1901A, 1901B (forming a first set of opposed blades) and Blades 1903A, 1903B (forming a second set of opposed blades). Holder 1900 further includes Body Portion 1905, from which each blade of the first set of opposed blades and each blade of the second set of opposed blades extends (wherein each blade of the first set of opposed blades and each blade of the second set of opposed blades is connected to Body Portion 1905 at the proximal end of the blade).

A number of Receiver Element Retaining Pins 1907 are disposed in each blade of the first set of opposed blades at a position adjacent the distal end each blade (wherein each Receiver Element Retaining Pin 1907 of the first set of opposed blades is configured to interface with a corresponding hole in the receiver element of the pedicle screw assembly to hold the receiver element of the pedicle screw assembly to the apparatus when each of the blades of the first set of opposed blades is in a closed position relative to one another).

Likewise a number of Receiver Element Retaining Pins 1907 are disposed in each blade of the second set of opposed blades at a position adjacent the distal end each blade (wherein each Receiver Element Retaining Pin 1907 of the second set of opposed blades is configured to interface with a corresponding hole in the receiver element of the pedicle screw assembly to hold the receiver element of the pedicle screw assembly to the apparatus when each of the blades of the second set of opposed blades is in a closed position relative to one another).

Of note, while the embodiment shown in these FIGS. 19-37 utilizes eight Receiver Element Retaining Pins 1907 (two pins per blade) any desired number of Receiver Element Retaining Pins 1907 may be utilized (for the sake of clarity, each of the Receiver Element Retaining Pins is identified in these FIGS. 19-37 by the same call out number—1907).

Holder 1900 further includes First Sliding Wedge 1909 disposed between each blade of the first set of opposed blades (wherein movement of the First Sliding Wedge 1909 from a first location relative to the first set of opposed blades (e.g., a more proximal location) to a second location relative to the first set of opposed blades (e.g., a more distal location) causes First Sliding Wedge 1909 to push each blade of the first set of opposed blades apart into an open position—see, e.g., FIG. 24).

Moreover, Holder 1900 further includes Second Sliding Wedge 1911 disposed between each blade of the second set of opposed blades (wherein movement of Second Sliding Wedge 1911 from a first location relative to the second set of opposed blades (e.g., a more proximal location) to a second location relative to the second set of opposed blades (e.g., a more distal location) causes Second Sliding Wedge 1911 to push each blade of the second set of opposed blades apart into an open position—see, e.g., FIG. 24).

Of note, the receiver element may (in this embodiment) be attached to Holder 1900 by: (a) movement of First Sliding Wedge 1909 from the first location relative to the first set of opposed blades (e.g., a more proximal location) to the second location relative to the first set of opposed blades (e.g., a more distal location) to cause First Sliding Wedge 1909 to push each blade of the first set of opposed blades apart into the open position (see, e.g., FIG. 24) and movement of Second Sliding Wedge 1911 from the first location relative to the second set of opposed blades (e.g., a more proximal location) to the second location relative to the second set of opposed blades (e.g., a more distal location) to cause Second Sliding Wedge 1911 to push each blade of the second set of opposed blades apart into the open position (see, e.g., FIG. 24); and (b) movement of First Sliding Wedge 1909 from the second location relative to the first set of opposed blades (e.g., a more distal location) back to the first location relative to the first set of opposed blades (e.g., a more proximal location) to allow each blade of the first set of opposed blades to flex back towards one another into the closed position (see, e.g., FIG. 23) and movement of Second Sliding Wedge 1911 from the second location relative to the second set of opposed blades (e.g., a more distal location) back to the first location relative to the second set of opposed blades (e.g., a more proximal location) to allow each blade of the second set of opposed blades to flex back towards one another into the closed position (see, e.g., FIG. 23).

Similarly, the receiver element may (in this embodiment) be released from the apparatus by movement of First Sliding Wedge 1909 from the first location relative to the first set of opposed blades (e.g., a more proximal location) to the second location relative to the first set of opposed blades (e.g., a more distal location) to cause First Sliding Wedge 1909 to push each blade of the first set of opposed blades apart into the open position (see, e.g., FIG. 24) and movement of Second Sliding Wedge 1911 from the first location relative to the second set of opposed blades (e.g., a more proximal location) to the second location relative to the second set of opposed blades (e.g., a more distal location) to cause Second Sliding Wedge 1911 to push each blade of the second set of opposed blades apart into the open position (see, e.g., FIG. 24).

Still referring to FIGS. 19-37, it is seen that Holder 1900 may include Knob 1913 for moving First Sliding Wedge 1909 between the first location relative to the first set of opposed blades (e.g., a more proximal location) and the second location relative to the first set of opposed blades (e.g., a more distal location) and for moving Second Sliding Wedge 1911 between the first location relative to the second set of opposed blades (e.g., a more proximal location) and the second location relative to the second set of opposed blades (e.g., a more distal location).

In the embodiment shown in FIGS. 19-37, Knob 1913 moves First Sliding Wedge 1909 and Second Sliding Wedge 1911 in unison with one another.

Further, in the embodiment shown in FIGS. 19-37, First Sliding Wedge 1909 and Second Sliding Wedge 1911 are attached to Knob 1913 as follows: (a) First Sliding Wedge 1909 is attached to Knob 1913 via Attachment Pin 1915A extending through: (i) Hole 1917A in First Sliding Wedge 1909; and (ii) Slot 1919A in Knob 1913; and (b) Second Sliding Wedge 1911 is attached to Knob 1913 via Attachment Pin 1915B extending through: (i) Hole 1917B in Second Sliding Wedge 1911; and (ii) Slot 1919B in Knob 1913.

Knob 1913 may be rotatable around a rotation axis defined by the proximal and distal ends of the blades such that when Knob 1913 is rotated to an unlocked position (see, e.g., FIGS. 25-33) Pins 1921A, 1921B in Body 1905 interface with Slots 1923A, 1923B in Knob 1913 to permit Knob 1913 to be movable axially along the rotation axis and when Knob 1913 is rotated to a locked position (see, e.g., FIGS. 34-37) Pins 1921A, 1921B in Body 1905 interface with Slots 1923A, 1923B in Knob 1913 to prohibit Knob 1913 from being movable axially along the rotation axis.

Further, as seen, for example, in FIGS. 26 and 35, one or more detent mechanisms (e.g., one or more spring detent mechanisms) may be associated with the unlocked/locked positions of Knob 1913 (e.g., to provide tactile feedback of locked/unlocked position).

Still referring to FIGS. 19-37, it is seen that at least a portion of the First Sliding Wedge 1909 may have a dovetail cross-section (wherein at least a portion of the First Sliding Wedge 1909 is disposed in a complementary dovetail groove formed between at least part of each blade of the first set of opposed blades) and that at least a portion of Second Sliding Wedge 1911 may have a dovetail cross-section (wherein at least a portion of Second Sliding Wedge 1911 is disposed in a complementary dovetail groove formed between at least part of each blade of the second set of opposed blades).

It is also seen that Cross-pin 1925A extends between each blade of the first set of opposed blades at a position adjacent the distal ends of the blades (wherein Cross-pin 1925A is disposed in Slot 1927A in First Sliding Wedge 1909) and that Cross-pin 1925B extends between each blade of the second set of opposed blades at a position adjacent the distal ends of the blades (wherein Cross-pin 1925B is disposed in Slot 1927B in Second Sliding Wedge 1911). Of note, use of such Cross-pins 1925A, 1925B may help prevent wedge pop-out and help maintain alignment of the blades).

It is also seen that First Sliding Wedge 1909 may include Prongs 1929A interfacing with Recesses 1931A in the first set of opposed blades and that Second Sliding Wedge 1911 may include Prongs 1929B interfacing with Recesses 1931B in the first set of opposed blades (see, e.g. detail of FIG. 22).

Of note, Prongs 1929A interfacing with Recesses 1931A may stop the blades of the first set of opposed blades from separating from one another when the First Sliding Wedge 1909 is at the first location relative to the first set of opposed blades (e.g., a more proximal location).

Similarly, Prongs 1929B interfacing with Recesses 1931B may stop the blades of the second set of opposed blades from separating from one another when the Second Sliding Wedge 1911 is at the first location relative to the second set of opposed blades (e.g., a more proximal location).

Moreover, when First Sliding Wedge 1909 is at the second location relative to the first set of opposed blades (e.g., a more distal location) Prongs 1929A may be displaced from Recesses 1931A to permit the blades of the first set of opposed blades to separate from one another.

Similarly, when Second Sliding Wedge 1911 is at the second location relative to the second set of opposed blades (e.g., a more distal location) Prongs 1929B may be displaced from Recesses 1931B to permit the blades of the second set of opposed blades to separate from one another.

In one specific example, each of the Receiver Element Retaining Pins 1907 may have a circular cross-section.

In another specific example, two Receiver Element Retaining Pins 1907 may be disposed in each blade of the first set of opposed blades and two Receiver Element Retaining Pins 1907 may be disposed in each blade of the second set of opposed blades.

In another specific example, the knob may include a hole therethrough for receiving a rod to enable the knob to be rotated with additional leverage applied via the rod (e.g., via mechanical advantage).

In another specific example, Slots 1933 may be provided (e.g., two slots—one slot on each side of the holder) to allow attachment of a spondolisthesis reduction device. In one example, this would be used in conjunction with a cannulated tube that would rest against the rod connected to the implanted screws and a distracter device with tips that mate to the head holder body and the cannulated tube.

Referring now to FIGS. 38A-38E, various view of Receiver Element 3800 according to an embodiment of the present invention are shown. As seen in these FIGS. 38A-38E, Receiver Element 3800 may include Holes 3803 (corresponding to each of the receiver element retaining pins in the holder device).

While a number of embodiments of the present invention have been described, it is understood that these embodiments are illustrative only, and not restrictive, and that many modifications may become apparent to those of ordinary skill in the art. For example, articulation may be provided between only one set of two blades (e.g., an upper set of blades or a lower set of blades) rather than between each blade of a first set and between each blade of a second set, as principally described. Further the pins may be attached via interference fit, welding, glue and/or any other desired mechanism. Further still, any steps described herein may be carried out in any desired order (and any additional steps may be added as desired and any steps may be deleted as desired).

What is claimed is:

1. An apparatus for releasably holding a receiver element of a pedicle screw assembly, comprising:
   a first set of opposed blades, each blade of the first set of opposed blades having a proximal end and a distal end;
   a second set of opposed blades, each blade of the second set of opposed blades having a proximal end and a distal end;
   a body portion from which each blade of the first set of opposed blades and each blade of the second set of opposed blades extends, wherein each blade of the first set of opposed blades and each blade of the second set of opposed blades is connected to the body portion at the proximal end of the blade;
   at least one receiver element retaining pin disposed in each blade of the first set of opposed blades at a position adjacent the distal end each blade, wherein each receiver element retaining pin of the first set of opposed blades is configured to interface with a corresponding hole in the receiver element of the pedicle screw assembly to hold the receiver element of the pedicle screw assembly to the apparatus when the each of the blades of the first set of opposed blades is in a closed position relative to one another;
   at least one receiver element retaining pin disposed in each blade of the second set of opposed blades at a position adjacent the distal end each blade, wherein each receiver element retaining pin of the second set of opposed blades is configured to interface with a corresponding hole in the receiver element of the pedicle screw assembly to hold the receiver element of the pedicle screw assembly to the apparatus when the each of the blades of the second set of opposed blades is in a closed position relative to one another;
   a first sliding wedge disposed between each blade of the first set of opposed blades, wherein movement of the first sliding wedge from a first location relative to the first set of opposed blades to a second location relative to the first set of opposed blades causes the first sliding wedge to push each blade of the first set of opposed blades apart into an open position; and
   a second sliding wedge disposed between each blade of the second set of opposed blades, wherein movement of the second sliding wedge from a first location relative to the second set of opposed blades to a second location relative to the second set of opposed blades causes the second sliding wedge to push each blade of the second set of opposed blades apart into an open position.

2. The apparatus of claim 1, wherein the receiver element is attached to the apparatus by:
   (a) movement of the first sliding wedge from the first location relative to the first set of opposed blades to the second location relative to the first set of opposed blades to cause the first sliding wedge to push each blade of the first set of opposed blades apart into the open position and movement of the second sliding wedge from the first location relative to the second set of opposed blades to the second location relative to the second set of opposed blades to cause the second sliding wedge to push each blade of the second set of opposed blades apart into the open position; and
   (b) movement of the first sliding wedge from the second location relative to the first set of opposed blades back to the first location relative to the first set of opposed blades to allow each blade of the first set of opposed blades to flex back towards one another into the closed position and movement of the second sliding wedge from the second location relative to the second set of opposed blades back to the first location relative to the second set of opposed blades to allow each blade of the second set of opposed blades to flex back towards one another into the closed position.

3. The apparatus of claim 1, wherein the receiver element is released from the apparatus by movement of the first sliding wedge from the first location relative to the first set of opposed blades to the second location relative to the first set of opposed blades to cause the first sliding wedge to push each blade of the first set of opposed blades apart into the open position and movement of the second sliding wedge from the first location relative to the second set of opposed blades to the second location relative to the second set of opposed blades to cause the second sliding wedge to push each blade of the second set of opposed blades apart into the open position.

4. The apparatus of claim 1, further comprising a control mechanism that moves the first sliding wedge between the first location relative to the first set of opposed blades and the second location relative to the first set of opposed blades and that moves the second sliding wedge between the first location relative to the second set of opposed blades and the second location relative to the second set of opposed blades.

5. The apparatus of claim 4, wherein the control mechanism moves the first sliding wedge and the second sliding wedge in unison with one another.

6. The apparatus of claim 5, wherein the control mechanism comprises a knob to which the first sliding wedge and the second sliding wedge are attached.

7. The apparatus of claim 6, wherein:
(a) the first sliding wedge is attached to the knob via a first attachment pin extending through: (i) a hole in the first sliding wedge, and (ii) a first slot in the knob; and
(b) the second sliding wedge is attached to the knob via a second attachment pin extending through: (i) a hole in the second sliding wedge, and (ii) a second slot in the knob.

8. The apparatus of claim 6, wherein the knob is rotatable around a rotation axis defined by the proximal and distal ends of the blades such that when the knob is rotated to an unlocked position at least one pin in the body interfaces with at least one slot in the knob to permit the knob to be movable axially along the rotation axis and when the knob is rotated to a locked position the pin in the body interfaces with the slot in the knob to prohibit the knob from being movable axially along the rotation axis.

9. The apparatus of claim 6, wherein the knob includes a hole therethrough for receiving a rod to enable the knob to be rotated with additional leverage applied via the rod.

10. The apparatus of claim 6, further comprising a first detent mechanism associated with the unlocked position and a second detent mechanism associated with locked position.

11. The apparatus of claim 1, wherein each of the receiver element retaining pins has a circular cross-section.

12. The apparatus of claim 1, wherein two receiver element retaining pins are disposed in each blade of the first set of opposed blades and two receiver element retaining pins are disposed in each blade of the second set of opposed blades.

13. The apparatus of claim 1, wherein at least a portion of the first sliding wedge has a dovetail cross-section, wherein at least a portion of the first sliding wedge is disposed in a complementary dovetail groove formed between at least part of each blade of the first set of opposed blades, wherein at least a portion of the second sliding wedge has a dovetail cross-section, and wherein at least a portion of the second sliding wedge is disposed in a complementary dovetail groove formed between at least part of each blade of the second set of opposed blades.

14. The apparatus of claim 1, wherein a first cross-pin extends between each blade of the first set of opposed blades at a position adjacent the distal ends of the blades, wherein the first cross-pin is disposed in a slot in the first sliding wedge, wherein a second cross-pin extends between each blade of the second set of opposed blades at a position adjacent the distal ends of the blades, and wherein the second cross-pin is disposed in a slot in the second sliding wedge.

15. The apparatus of claim 1, wherein the first sliding wedge comprises a first locking mechanism interfacing with each blade of the first set of opposed blades to stop the blades of the first set of opposed blades from separating from one another when the first sliding wedge is at the first location relative to the first set of opposed blades and wherein the second sliding wedge comprises a second locking mechanism interfacing with each blade of the second set of opposed blades to stop the blades of the second set of opposed blades from separating from one another when the second sliding wedge is at the first location relative to the second set of opposed blades.

16. The apparatus of claim 15, wherein the first locking mechanism interfaces with each blade of the first set of opposed blades to permit the blades of the first set of opposed blades to separate from one another when the first sliding wedge is at the second location relative to the first set of opposed blades and wherein the second locking mechanism interfaces with each blade of the second set of opposed blades set to permit the blades of the second set of opposed blades to separate from one another when the second sliding wedge is at the second location relative to the second set of opposed blades.

17. The apparatus of claim 16, wherein the first locking mechanism comprises a first pair of prongs interfacing with a first pair of complementary recesses in the first set of opposed blades and wherein the second locking mechanism comprises a second pair of prongs interfacing with a second pair of complementary recesses in the second set of opposed blades.

18. An apparatus for releasably holding a receiver element of a pedicle screw assembly, comprising:
a set of opposed blades, each blade having a proximal end and a distal end;
a body portion from which each blade of the set of opposed blades extends, wherein each blade of the set of opposed blades is connected to the body portion at the proximal end of the blade;
at least one receiver element retaining pin disposed in each blade of the set of opposed blades at a position adjacent the distal end each blade, wherein the receiver element retaining pin is configured to interface with a corresponding hole in the receiver element of the pedicle screw assembly to hold the receiver element of the pedicle screw assembly to the apparatus when each of the blades of the set of opposed blades is in a closed position relative to one another; and
a sliding wedge disposed between each blade of the set of opposed blades, wherein movement of the sliding wedge from a first location to a second location causes the sliding wedge to push each blade of the set of opposed blades apart into an open position.

19. The apparatus of claim 18, wherein the receiver element is attached to the apparatus by:
(a) movement of the sliding wedge from the first location to the second location to cause the sliding wedge to push each blade of the set of opposed blades apart into the open position; and
(b) movement of the sliding wedge from the second location back to the first location to allow each blade of the set of opposed blades to flex back towards one another into the closed position.

20. The apparatus of claim 18, wherein the receiver element is released from the apparatus by movement of the sliding wedge from the first location to the second location to cause the sliding wedge to push each blade of the set of opposed blades apart into the open position.

* * * * *